United States Patent
Gill et al.

(10) Patent No.: US 10,532,093 B2
(45) Date of Patent: Jan. 14, 2020

(54) THERMOSTABLE FREEZE DRIED ROTAVIRUS VACCINE FORMULATION AND PROCESS TO PREPARE THEREOF

(71) Applicant: MSD WELLCOME TRUST HILLEMAN LABORATORIES PVT. LTD., New Delhi (IN)

(72) Inventors: Davinder Gill, New Delhi (IN); Madhu Madan, Haryana (IN); Sachin Kale, Haryana (IN); Tarun Sharma, New Delhi (IN); Nidhi Shukla, Uttar Pradesh (IN); Deepa Sikriwal, New Delhi (IN); Robert Evans, Sourderton, PA (US)

(73) Assignee: MDS WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 112 days.

(21) Appl. No.: 15/327,142

(22) PCT Filed: Jul. 16, 2015

(86) PCT No.: PCT/IB2015/055383
§ 371 (c)(1),
(2) Date: Jan. 18, 2017

(87) PCT Pub. No.: WO2016/009381
PCT Pub. Date: Jan. 21, 2016

(65) Prior Publication Data
US 2017/0165354 A1 Jun. 15, 2017

(30) Foreign Application Priority Data
Jul. 18, 2014 (IN) .......................... 2037/DEL/2014

(51) Int. Cl.
| | | |
|---|---|---|
| *A61K 39/15* | (2006.01) | |
| *A61K 39/12* | (2006.01) | |
| *A61K 9/08* | (2006.01) | |
| *A61K 9/19* | (2006.01) | |
| *A61K 47/02* | (2006.01) | |
| *A61K 47/18* | (2017.01) | |
| *A61K 47/22* | (2006.01) | |
| *A61K 47/26* | (2006.01) | |
| *A61K 47/32* | (2006.01) | |
| *A61K 39/00* | (2006.01) | |

(52) U.S. Cl.
CPC ................ *A61K 39/15* (2013.01); *A61K 9/08* (2013.01); *A61K 9/19* (2013.01); *A61K 39/12* (2013.01); *A61K 47/02* (2013.01); *A61K 47/183* (2013.01); *A61K 47/22* (2013.01); *A61K 47/26* (2013.01); *A61K 47/32* (2013.01); *A61K 2039/70* (2013.01); *C12N 2720/12321* (2013.01); *C12N 2720/12334* (2013.01)

(58) Field of Classification Search
None
See application file for complete search history.

(56) References Cited

U.S. PATENT DOCUMENTS

| | | | | |
|---|---|---|---|---|
| 6,616,931 B1 * | 9/2003 | Burke | .................... | A61K 39/15 424/215.1 |
| 8,322,637 B2 * | 12/2012 | Nur | .......................... | A61K 9/14 241/29 |
| 2011/0243988 A1 * | 10/2011 | Ohtake | ................. | A61K 39/165 424/212.1 |
| 2011/0293717 A1 * | 12/2011 | Swatschek | ........... | A61K 9/1623 424/465 |
| 2012/0107356 A1 * | 5/2012 | Vadrevu | .................. | A61K 39/15 424/215.1 |

FOREIGN PATENT DOCUMENTS

WO  WO 2010/146598  * 11/2009

* cited by examiner

Primary Examiner — Shanon A. Foley
Assistant Examiner — Myron G Hill
(74) Attorney, Agent, or Firm — W&C IP

(57) ABSTRACT

The present invention relates to a thermostable freeze dried rotavirus vaccine formulation and the process of preparing the same. More specifically the present invention discloses multivalent thermostable liquid, powder or cake based rotavirus vaccine formulation prepared using the freeze drying process, such that the said vaccine formulation possess improved heat-stability, easy to use and transport and highly affordable thereby meeting the requirements of developing and low income country's vaccination program. The said freeze dried rotavirus vaccine formulation along with reconstitution buffer is so engineered to be suitable for filling in appropriate packaging containers/ closures so designed such that they reduce the logistics requirement for storage.

27 Claims, 6 Drawing Sheets

THERMOSTABLE FREEZE DRIED ROTAVIRUS VACCINE FORMULATION AND PROCESS TO PREPARE THEREOF

FIELD OF THE INVENTION

The present invention relates to a thermostable freeze dried rotavirus vaccine formulation and the process of preparing the same. More specifically the present invention discloses improved thermostable rotavirus vaccine formulation in dried cake or dried powder form. The present invention also relates to rotavirus vaccine having improved heat-stability and easy to use and transport. The said vaccine meets the requirements of developing and low income country's vaccination program.

BACKGROUND OF THE INVENTION

It is well established that rotavirus is the leading cause of severe diarrhoea among infants and young children. It is estimated that globally 0.5-0.6 million children under the age of 5 die annually due to rotavirus diarrhea and another 2 million are hospitalized. About 90% to 95% of these deaths occur mainly in developing countries.

Rotavirus is highly contagious and resistant regardless of water quality and available sanitation nearly every child in the world is at risk of infection. Vaccination has been proven to be the most effective means of prophylaxis for rotavirus infection. International research data suggests that current rotavirus vaccines have 85% to 95% efficacy against severe rotavirus gastroenteritis (RVGE). In light of this, the World Health Organization (WHO) on 5th Jun. 2009 recommended that rotavirus vaccine must be included in all the national immunization programs.

However, there are concerns while using the same in developing countries where 90% to 95% deaths occur due to rotavirus infection, and where access to treatment is also limited. The two major concerns faced by developing countries are 1) lower efficacy of rotavirus vaccines in developing and low resource countries and 2) programmatic suitability as well as cost of current available vaccines.

It has been reported that more than 2.4 million child deaths can be prevented by 2030 by accelerating access to rotavirus vaccines. If these vaccines are used in 'Global Alliance for Vaccine and Immunization (GAVI)-countries, it could prevent an estimated 180,000 deaths and avert 6 million clinic or hospital visits each year, thereby saving US $68 million annually in the treatment cost.

However, in order to increase the reach of the rotavirus vaccines in these regions, new programmatically suitable vaccines must be developed and qualified for global use. Programmatic suitability is a new process developed by the WHO relating to the prequalification of vaccines with the aim to address needs of developing country and facilitating universal immunization without requiring additional investments in cold chain capacity, human resources, waste disposal facilities, etc. This process outlines Mandatory, Critical Unique, Innovative and Preferred programmatic suitability characteristics that a vaccine must possess for WHO prequalification.

It is well known in the art that the vaccines must be stored and transported at refrigerator temperature maintained in the range of 2° C. to 8° C. Further, it is also well known that vaccines must be administered immediately after being removed from refrigeration. Usually a WHO prequalified vaccine is stable for up to 24 to 36 months at 2° C. to 8° C.

The current WHO prequalified rotavirus vaccines are stable only for a limited duration at a particular temperature as mentioned above. Studies indicate that if the currently available vaccine, for example, Rotateq® vaccine is inadvertently exposed or stored at temperatures above 8° C., the potency is maintained for the maximum exposure of 48 hours (h) at 9° C. to 25° C. or for a bare 12 hours at 26° C. to 30° C. However, if RotaTeq® vaccine is exposed to temperatures above 30° C., or if the time mentioned above has lapsed, the vaccine has to be discarded since it has lost its potency. There is limited data to suggest that if the vaccine is inadvertently exposed to temperatures below 0° C., the potency of the vaccine is maintained. Another, currently available freeze dried vaccine i.e. Rotarix vaccine exhibit stability with a shelf life of 36 months at 2° C.-8° C.

However, irrespective of the stability profile both vaccines are required to maintain the cold chain during transport. It is very difficult to maintain the cold chain required to conserve the vaccine potency particularly in developing and low income countries resulting in large amount of vaccine being wasted and in worst case scenario endangering the lives of potential recipients. The WHO estimates that nearly half of freeze-dried and quarter of liquid vaccines are wasted each year. One of the biggest contributors to this wastage is disruption of the cold chain. The GAVI Alliance, which supports developing countries in their vaccination efforts, estimates that half of the healthcare facilities in the these countries have no electricity supply at all, with only 10% having a reliable electricity supply; an obligatory requirement for cold chain operation. For example, in India, a country which has largest burden of rotavirus disease, a National Cold Chain Assessment-2008 report by UNICEF in collaboration with Govt. of India, state governments and WHO, concluded that management of entire cold chain infrastructure and logistics suffers from acute shortage equipment, infrastructure and of trained manpower.

Thus there is a great demand for thermostable vaccines. Many existing vaccines do exhibit some degree of thermostability. However, the existing vaccines possess shorter period of thermostability (e.g. VVM 7 or VVM 14) which fails to address the issue and therefore, is difficult to reach to developing world. For example, in India, like most developing world, uses a multi-tier vaccine store network which receives, stores and supply huge quantity of vaccines with all vaccines requiring storage in a temperature range of +2° C. to +8° C. In this journey vaccines spend at least an year from manufacturer to recipients, putting huge burden on cold chain which is inadequate. Since cold chain is the most important component to ensure the quality of vaccine, developing a thermostable vaccine that could be transported and stored outside cold chain for extended period of time is on high priority for healthcare sector. This is particularly more important for freeze dried vaccine since it bears higher wastage burden.

The thermostability feature is also beneficial to vaccine logistics in regions of the world where ambient extremes of temperatures exceed 40° C. and where cold chain is not available nearby.

The presently available freeze dried vaccines does not possess enough thermostability profile suitable for storage outside cold chain for any meaningful amount of time and these have to be stored and transported under refrigeration. Hence there is a current lack of vaccines and the formulation processes that endow sufficient thermostability to a vaccine is therefore a significant barrier to global vaccination efforts, particularly for live attenuated vaccines. Understanding the possible mechanisms of destabilisation for the vaccine of interest and adjusting the vaccine formulation as well as tuning the process parameters is essential for quenching those mechanisms is essential for designing successful freeze drying process.

Although freeze drying confers extended stability on vaccine formulations, it incurs higher manufacturing costs. The cost of freeze drying is directly correlated to the scale which in turn is defined by surface area of the shelves. This can make thermostable freeze dried vaccine unattractive in terms of costs over its thermolabile liquid vaccine formulations. Thus there also arises a need for designing a cost-effective thermostabilization process.

Further, most of the existing solid forms of vaccines are packaged in separate containers/components and require syringe and a vial as well as other complex and costly mechanisms for reconstitution and administration. This causes difficulty in the administration of vaccine and also greatly increases the footprint of the vaccine by overburdening the cold chain. This also in turn increases the shipping and distribution challenges, logistics for storage and is prone to potentially fatal reconstitution errors like buffer/vaccine mismatch, contamination, administration of wrong volumes etc. Thus there is a need for innovative form of vaccine that offers flexibility in its filling in the improved containers/closures that improves logistics as well as administration of the vaccine.

The U.S. Pat. No. 6,616,931 (WO2002/011540) describes rotavirus vaccine stability in formulations differing in buffers, divalent metal ions, sugar and polyanions, surfactants, amino acids in both liquid and freeze dried forms. These formulations however failed to yield thermostability above 22° C. to 30° C. for any significant amount of time. It is also quoted that freeze drying of rotavirus vaccines can result in loss of viral titer which in turn result in low yields, and the potency below required levels resulting ineffective immunization by the freeze dried vaccine formulation. A reconstitution buffer is also reported for freeze dried formulations which provides additional acid-neutralizing capacity needed for buffering of gastric acid. This patent also discloses that incubation for 30 minutes at 37° C. or 2 hours at 30° C. of the reconstituted freeze dried formulation is subject to losing potency at room temperatures.

GlaxoSmithkline's U.S. Pat. No. 7,285,280 discloses a live attenuated rotavirus vaccine formulation. The vaccine formulation is freeze dried with Calcium Carbonate present as the antacid to be reconstituted with aqueous solution prior to administration. Alternatively, this patent also claim a vaccine formulation as a quick dissolving tablet in freeze dried form to be directly placed on the tongue of an infant/child wherein the rotavirus antigen. Another GSK's U.S. Pat. No. 8,192,747 claims a liquid oral rotavirus formulation comprising live attenuated rotavirus antigen, a sugar a carboxylate and a carboxylic acid, adipic acid along with calcium ions, wherein the composition has an antacid capacity of at least 12 minutes.

The U.S. patent application 2012/0107356 describes vaccine formulation prepared without stabilizer with enhanced viral titers, shelf life and the thermostability. The shelf life can be further extended with addition of stabilizers. In spite of this remarkable thermostability the current licensed vaccine is a liquid form that requires storage at −20° C. Furthermore, the ingredients include proteins which, even if produced using processes supporting high yields, have a cost implications for formulations. For a vaccine to be broadly adopted in low income regions it is crucial to keep the cost of vaccine and its components such as stabilizers low. It is also crucial from the regulatory and safety point of view that excipient's and stabilizers used should contain neither substances of animal origin nor contain animal component. Indeed in some countries, it is not desirable for cultural and religious reasons as well.

International patent application no. PCT/US2008/011169 discloses freeze drying of the rotavirus formulations for preservation of rotavirus by using divalent cations as stabilizers such as $Zn^{2+}$ and $Ca^{2+}$ in liquid Rotavirus formulations. These fortified formulations demonstrated superior stability as is evidenced by the fact that the freeze drying did not cause instability to the vaccine. Using live G1 rotavirus strain as a representative serotype, freeze drying was carried out with different formulation compositions. Process loss for freeze drying was negligible to less than 0.2 log ffu/mL and the decrease in the initial titer was negligible to 0.7 log ffu/mL respectively after 2 months of storage at 37° C. The titer decrease was negligible after 3 months of storage at 4° C. and at 25° C. (<0.1 log ffu/mL).

One of the remarkable observation in the International patent application no. PCT/US2008/011169 was that the presence of $Zn^{2+}$ in liquid rotavirus vaccines enhances the stability of virus viability, but in the U.S. Pat. No. 6,616, the presence of $Zn^{2+}$ accelerated inactivation of rotavirus serotypes constituting RotaTeq. This observation however was not attributed to presence of divalent cations solely but to the concomitant presence of sucrose and pH.

For freeze drying, only conclusion drawn here was that presence of $Zn^{2+}$ did not destabilize the rotavirus, either during the freeze drying process or during its storage at an elevated temperature. Thus the role of divalent cations for stabilization of rotavirus vaccine is not clear. It is also not clear that conclusions and claims based on experiments on single rotavirus serotype would be applicable to all rotavirus serotypes especially those constituting a multivalent rotavirus vaccine. Thus there is a need for rational design of formulation for arriving at an optimal and effective formulation(s).

Therefore, to cater to the abovementioned problems there is a need of a mono-dose, thermostable, cost effective vaccine which will be a great advantage to the vaccination program of developing and low income countries.

Thus, the present invention describes a thermostable vaccine with higher titre value and that could be transported in non-refrigerated supply chain significantly reducing the cost and complications associated with transporting vaccine to remote corners of the world.

OBJECT OF THE INVENTION

The main object of the invention is to provide an improved thermostable freeze dried rotavirus vaccine formulation.

Another object of present invention is to provide an improved freeze drying process to obtain an improved thermostable freeze dried rotavirus vaccine formulation.

Yet another object of the present invention is to provide an improved thermostable freeze dried rotavirus vaccine formulation that obviates or significantly minimizes potency losses at elevated temperatures for a longer period thereby reducing dependency on refrigeration and cold chain maintenance.

Yet another object of the invention is to provide an efficacious and economically viable thermostable freeze dried rotavirus vaccine formulation of higher titre value.

Yet another object of the invention is to provide a process of preparing thermostable freeze dried rotavirus vaccine comprising the strains of live rotaviruses selected from bovine, rhesus, human, ovine, rhesus/human reassortants, or bovine/human reassortants.

Yet another object of the invention is to provide a process of preparing thermostable freeze dried rotavirus vaccine comprising the strains of monovalent and/ or multivalent rotavirus.

Yet another object of the invention is to provide rotavirus vaccine formulation along with a reconstitution buffer either individually or in combination providing acid neutralization capacity sufficient to protect live viruses from gastric acid.

Yet another object of present invention is to prepare an improved thermostable freeze dried rotavirus vaccine formulation possessing properties ideal for filling and administration by drug delivery devices preferably oral delivery devices.

Yet another object of the invention is to provide cost effective rotavirus vaccine with reduced footprint, which is stable at higher temperature, easy-to-use, easy-to-transport and meets the requirements of low income and developing world countries.

SUMMARY OF THE INVENTION

Accordingly, the present invention relates to a thermostable freeze dried rotavirus vaccine formulation and process to prepare thereof. The said process relates to stabilization of the rotavirus vaccine by using freeze drying methodology to generate dehydrated form of vaccine. The dehydration is accomplished by using freeze drying methodology in the presence of excipients comprising various stabilizers. Said stabilizers convert unstable water interactions with stable interactions of formulation ingredients thereby affording thermostability to the vaccine component at low temperatures, at room temperature and at higher temperatures.

The thermostable freeze dried rotavirus vaccine of present invention comprises of strains selected from monovalent or multivalent rotaviruses or their combinations and the said live attenuated viruses are selected from bovine, rhesus, human, ovine, rhesus/human reassortants, or bovine/human reassortants.

The thermostable rotavirus vaccine of present invention has a potential to retain potency at high temperatures frequently encountered in regions where majority of rotavirus burden exists and has potential to partially or completely eliminate the vaccine cold chain dependence.

The present invention provides an economical freeze drying process wherein freeze drying is accomplished in bulk at multiples of virus concentrations thereby reducing the production cost.

The present invention provides a thermostable freeze dried rotavirus vaccine that offers flexibility of packaging in diverse container /closures such as vials supplied with a prefilled syringe with reconstitution buffer, or two vials with vaccine and buffer respectively and an adapter and syringe or a single container closure that is comprised of a dual chamber pouch with a frangible seal that could be broken upon squeezing between fingers on reconstitution buffer chamber allowing solid vaccine and reconstitution buffer to mix.

Thus the present invention discloses a thermostable freeze dried rotavirus vaccine formulation and process of preparing the said vaccine. The said vaccine possesses improved heat-stability, reduced footprint, low-cost of production and transportation and easy to use and transport.

DETAILED DESCRIPTION OF THE INVENTION

Figure 1:
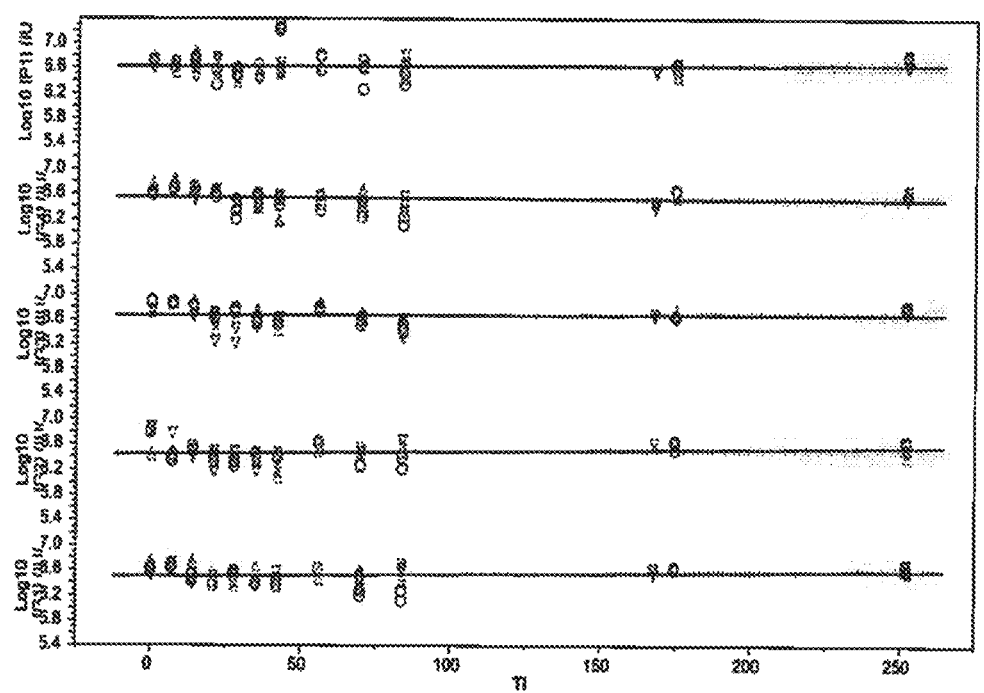
FIG. 1: Stability data of freeze dried formulation 1004c in vials containing five human bovine serotypes (G1, G2, G3, G4 and P1) for N=1 (○), N=2 (Δ) and N=3 (□) at 2° C. to 8° C. storage conditions.

In order to obviate the aforementioned drawbacks in the existing prior art, the present invention relates to a thermostable freeze dried rotavirus vaccine formulation and the process of preparing the same. More specifically the present invention discloses an improved thermostable dried cake or dried powder form of rotavirus vaccine formulation prepared by using an improved freeze drying process. The present invention also relates to liquid or solid rotavirus vaccine formulation prepared using reconstitution of dried cake or dried powder form of vaccine formulation, such that said vaccine formulation have improved heat-stability, easy to transport and use and is affordable. Therefore, said vaccine meets the requirements of developing and low income country's vaccination program.

The invention uses the process of freeze drying for removing water moiety, one of the major sources of instability for aqueous rotavirus vaccine. The water moiety is extracted from the liquid rotavirus vaccine formulation either for individual virus or serotype, or in combination of multiple rotavirus serotypes to form dehydrated thermostable vaccine formulation. These methods of freeze drying results in achieving moisture content below 3.0 percent approximately thereby preventing degradation pathways in rotavirus serotypes associated with the presence of excess water.

Before the preferred embodiment of the present invention is disclosed, it is understood that this invention is not limited to the particulars materials described, as these may vary. It is also understood that the terminology used in herein is for the purpose of describing the particular embodiment only, and is not intended to limit the scope of the present invention in any way.

It must be noted that as used herein, the singular forms "a", "an" and "the" include plural reference unlike the context clearly dictates otherwise, unless defined otherwise, all technical and scientific terms used herein have the same meaning as commonly understood by one of ordinary skill in the art to which this invention belongs.

Accordingly, in a preferred embodiment, dehydration is accomplished using freeze drying process in presence of excipients including stabilizers, substituting unstable water interactions with stable interactions of stabilizing ingredients.

In one of the embodiment, the methodology of Design-of-Experiment (DoE) is employed for identification of the potential excipients, their concentrations and combinations thereof that are likely to have a significant impact on the potency loss of viruses in the vaccine formulation during freeze-drying process and other manufacturing steps and subsequent storage for determining the stability loss. In some cases, to minimize number of experiments, successive fractional factorial DoE have also been employed.

The suitability of potential excipients, their concentrations and combinations thereof is determined by various biophysical methods, for example, Differential Thermal Analysis (DTA), Differential Scanning calorimetry (DSC), Freeze Drying Microscopy (FDM) and Impendence measurements. Further, direct potency is also measured by using various methods,for example, Multivalent QPCR-Based Potency Assay (M-QPA) that permits the specific quantitation of each individual reassortant virus in the presence of the other four reassortant viruses. The biophysical methods give an indication of process suitability such as e.g. time and energy inputs required and the latter potency measurement methods gives an indication of the effect of excipients including stabilizers on the potency during processing and subsequently during storage. In some cases, potency change after repeated freeze-thawing of the virus in presence of DoE compositions followed by incubation at elevated temperature i.e. at 25° C. for extended period of time for at least 24 hours and a maximum of up to one week have also been used.

The excipients including various stabilizers are selected from, but not limited to (a) lyoprotectants such as Sucrose, Trehalose, Sorbitol and Lactose, (b) divalent cation more particularly divalent ionic structural stabilizers such as Zn (II) and Ca (II); (c) buffering agents such as HEPES, Tris, Phosphate, Citrate or Histidine; and (d) salts such as Sodium Chloride (NaCl), Magnesium chloride, Potassium cholride; (e) bulking agents such as Polyvinylpyrrolidone(PVP), Dextran,Mannitol; (0 activating agents including L-Arginine and/or Glycine and (g) dispersants such as Tween (e.g. Tween 20 and Tween 80).

In a preferred embodiment, the thermostable freeze dried vaccine preparation contain, lyoprotectants in the range of 1.2% w/v to 6.0% w/v, divalent cations like Zn (II) and Ca (II) in the range of 0 mM to 2 mM, salt is in the range of 0 mM-50 mM, buffering agents in the range of 10 mM to 50 mM, bulking agent in the range of 2% to 6% w/v, activating agents in the range of 10 mM to 100 mM, dispersants in the range of 0% w/v to 0.02% w/v, In yet another preferred embodiment, excipients including stabilizers, especially the buffering system, are so selected to allow maximum solubility to divalent ions, such as Zn (II) and Ca (II), which are principally required for maximum process stability and also play role in storage stability of rotavirus at elevated temperatures for extended period of time.

In yet another embodiment, the rotavirus vaccine formulation described in this invention can include live attenuated rotavirus of human-bovine reassortment i.e. G1, G2, G3, G4 and P1 as well as other live attenuated rotaviruses from bovine, rhesus, human, bovine, rhesus/human reassortants, or bovine/human reassortants. The other examples of viruses used in this invention, without limitation, may also include other live attenuated viruses including measles, noroviruses, polio and other monovalent or multivalent rotaviruses.

In yet another embodiment, particularly preferred freeze dried vaccine is prepared using 54 hour freeze drying cycle or 70 hour freeze drying cycle in vials and trays respectively. In some cases, the freeze drying cycle can be appropriately modified using inputs (glass transition temperature $T_g$' and eutectic melting temperature; $T_{eu}$) from various biophysical methods mentioned above and potency losses from M-QPA. In all aspects of invention, freeze drying using above optimized parameters and said compositions results in dried cake or dried solid powder with the residual moisture content of less than 3.0%. The said reduction in residual moisture to below 3% content results in preventing thermal degradation pathways associated with presence of water. The said rotavirus vaccine preparations can be obtained using any appropriate freeze drying method.

In a preferred embodiment, freeze drying formulation ingredients in composition and concentration are selected based on Potency and biophysical measurements to arrive at a formulation affording optimal freeze drying parameters and times with no more than $Log_{10}$=[0.2] process loss for the said virus serotypes.

In yet another embodiment, said rotavirus vaccine formulation can be freeze dried in vials in a monodose and/or multidose formulations and the said vaccine is reconstituted with the provided reconstitution buffer prior to administration.

In yet another embodiment, the said rotavirus vaccine formulation is freeze dried in bulk using commercially available freeze drying trays like GORE® LYOGUARD® Freeze-Drying Tray or stainless steel trays.

In yet another preferred embodiment, said rotavirus vaccine formulation is freeze dried in bulk for example rotavirus vaccine with 5-10 fold higher titers than the clinically relevant specifications are freeze dried thus reducing both the size and number of batches and thereby reducing the overall cost of production.

In order to obtain a powder suitable for filling in the container closure for particularly monodose container, the bulk freeze dried material is milled resulting in the milled freeze dried powder with particle size of $D_{90}$ value not less than 250 µm. The milling unit process can be accomplished using appropriate milling methods including but not limited to Sieve milling, Hammer milling, Conical sieve Milling, Ball milling and Roller milling at temperatures ranging from 0° C. to 25° C.

In yet another embodiment, the milled freeze dried powder can be blended with suitable blending agents selected from but not limited to PVP K25, PVP K40, sucrose, mannitol, maltodextrin with DE generally ranging from 4 to 20, fructose, glucose, lactose or placebo formulation of same composition or the combinations thereof. The said combinations are so prepared to obtain a powdered dosage form having rotavirus titers equal to clinically relevant minimal concentrations or any desired release specification as well as to engineer powder properties acceptable for accurate and precise powder filling in the predetermined packaging containers.

In yet another embodiment, the freeze drying is performed either at clinically relevant specification or at higher titre of rotavirus scales (5× in glass vials or in bulk using stainless steel trays with a process loss of not more than $Log_{10}$=[0.2], cumulative potency (process and stability) losses for the freeze dried rotavirus vaccine serotype in any combination do not exceed $Log_{10}=0.5$ irrespective of factors such as starting fill, serotype, process scale, and combinations thereof at 37° C.±2° C. (RH 75%±5.0%) for at least 30, 90 or 180 days and a cumulative potency (process and stability) losses for the freeze dried rotavirus vaccine serotype in any combination do not exceed $Log_{10}=0.5$ irrespective of the factors irrespective of factors such as starting fill, serotype, process scale, and combinations thereof at 45° C.±2° C. (RH 75%±5.0%) for at least 30, 90 or 120 days.

Rotavirus is acid-labile and gets rapidly inactivated with a half-life of less than 12 minutes at pH 2.0. The rotavirus vaccines are intended to be administered orally, it is crucial to protect rotavirus which may get inactivated by gastric acid present in stomach. The effective way for administering such vaccines is to use antacids or neutralizing buffers before or in combination with the oral vaccine.

In yet another embodiment of the present invention, special provisions are employed to protect the vaccine from stomach acid after oral administration, stomach acid neutralization is accomplished by administering the vaccine with buffering agent with better Acid Neutralization Capacity (ANC). The buffering/antacid component are selected from but not limited to HEPES, Trisodium citrate dihydrate, histidine, calcium carbonate, sodium carbonate, potassium carbonate, sodium bicarbonate, calcium bicarbonate, potassium bicarbonate, aluminum hydroxide, sodium dihydrogen phosphate monohydrate or magnesium hydroxide or combinations thereof.

In yet another embodiment of the present invention, said vaccine formulation is milled and and blended with blending agent and/or buffering agent imparting desired ANC which is in the range of 0.3 mEq/ dose to 1.0 mEq/dose of vaccine powder and moisture content is below 3%.

In yet another embodiment of the present invention, said vaccine formulation is reconstituted with a reconstitution buffer just before oral administration that imparts desired ANC which is in the range of 0.3 mEq/dose to 1.0 mEq/ dose of vaccine.

In another embodiment, to provide the palatability to the formulation, sugars are added in the concentration in the range of 0% w/v to 60% w/v to reconstitution buffer. The sugars are selected from but not limited to lactose, glucose, sucrose, fructose or the combinations thereof.

In all aspects of the present invention vaccine formulations are in dry form i.e. Freeze dried cake/powder, milled dried powder or milled and blended freeze dried powder. The said above formulations so obtained do not exceed potency losses exceeding $Log_{10}=[0.5]$ when stored at 5° C.±3° C. for at least 9 months that may be statistically extrapolated to 2 years) and at 37° C. or 45° C. for at least 18 weeks.

In all aspects of the present invention said powdered vaccine formulations are administered orally by reconstituting with either said reconstitution buffer when blended solely with blending agent or with water for Injection when blended with blending agent and with buffering agents having desired ANC.

Yet another aspect of the present invention provides aseptically reconstituted vaccine preparation that does not result in overall (process+stability) virus potency losses exceeding $Log_{10}=[0.5]$ when re-constituted in appropriate aqueous reconstitution buffer and stored at 2° C.-8° C. for 48 h.

In yet another embodiment of the present invention, the glass transition temperature (Tg) of milled vaccine is more than 47° C. to provide the thermal stability at higher temperature storage conditions.

In yet another embodiment, the powdered vaccine formulation is dispensed in the final packaging container/closures including sachet or vials supplied with separate reconstitution buffer for reconstitution.

Thus, said vaccine formulation have improved heat- stability, easy to transport and use and is affordable, hence said vaccine meets requirements of developing and low income country's vaccination program.

EXAMPLES

The following examples illustrate but do not limit the scope of this invention.

Example 1

Thermostabilization of Rotavirus Serotypes using Freeze Drying Process

Study 1: Selection of Excipients Including Stabilizers:

To identify among the potential ingredients, their concentrations and combinations thereof that are likely to have a significant impact on the stability of rotavirus during freeze-drying process including further processing steps (process loss) and storage (stability loss) as well as to support optimal and economical freeze-drying process, the methodology of Design-of-Experiment (DoE) is applied. The G1 strain of rotavirus is used as representative strain to report on the virus potency changes. To minimize number of experiments, successive fractional factorial designs are used.

The fractional factorial designs are limited to the 8 factors as shown in the Table 1 and Table 2.

TABLE 1

Various stabilizers and their concentrations used to design DoE formulations

| | Buffer | NaCl | Sugar/Bulking Agent | Amino-acids | | Activating agents | | Dispersant |
|---|---|---|---|---|---|---|---|---|
| Factor | 1 | 2 | 3 | 4 | 5 | 6 | 7 | 8 |
| Excipient | Tris/*Phos/ HEPES (mM) | NaCl (mM) | **Sugar | L-Arg (mM) | Gly (mM) | $CaCl_2 \cdot 2H_2O$ (mM) | $ZnCl_2$ (mM) | Tween (%) |
| Low level (−1) | 10 | 0 | 1.2/2 | 10 | 0 | 0 | 0 | 0 |
| Mid level (0) | 25 | 25 | 3/3 | 50 | 50 | 1 | 1 | 0.01 |
| High level (1) | 50 | 50 | 4/4.8 | 100 | 100 | 2 | 2 | 0.02 |

*Phos = phosphate; **mannitol, dextran or PVP

TABLE 2

Combinations of buffer and bulking agents used to design DoE formulations

| Combination | 1 | 2 | 3 | 4 | 5 | 6 | 7 | 8 | 9 |
|---|---|---|---|---|---|---|---|---|---|
| Buffer | *Phos | *Phos | *Phos | HEPES | HEPES | HEPES | Tris | Tris | Tris |
| Bulking agent | ***Dex | PVP | **Man | ***Dex | PVP | **Man | ***Dex | PVP | **Man |

*Phos = Phosphate; Man = Mannitol; *Dex = Dextran

To further simplify the screening design, one buffer and one combination of sugar and bulking agent at a time is selected in a step by step approach. This fractional factorial design yielded total 19 experiments per combination wherein the concentration of buffering agent, salt, sugar: bulking agent ratio, amino acids, activating agent and dispersant are varied. To test the ability of the stabilizer combination for optimal freeze-drying process design and for supporting virus stability during freeze-drying, following screening experiments are conducted:

(a) Differential Thermal Analysis, Freeze Drying Microscopy and Impendence measurements are conducted on placebo compositions to determine critical temperatures influencing freeze-drying process. The mannitol containing DoE set is omitted in initial screening as these formulations required longer freeze-drying cycles.

(b) Freeze-thaw (FT) studies are conducted wherein, G1 serotype at a concentration of 2.0E+07 IU/ml, is subjected to 5 cycles of freezing and thawing followed by incubation at 25° C. for one week. From these experiments, it is observed that sucrose: PVP containing combinations retained much better potency as compared to sucrose: dextran containing combinations for G1 strain.

(c) The selected best performing formulations in terms of potency are evaluated further in actual freeze drying experiments with G1 at a concentration of 7.3 log/mL of aqueous feed as shown in Table 3. The 1 ml liquid feed from these selected formulations is dispensed into 5 ml capacity glass vials and freeze dried using 82 hour to 110 hour cycle characterized by;

i. Precooling the pre lyophilized liquid to 10° C. to 12° C. and loaded into the lyophilizer.

ii. freezing the pre lyophilized liquid at −40° C. for 3 hour-4 hour (with ramp down of 4° C. to −40° C. within 0.5 to 2.0h) followed by annealing at −20° C. for another 2 h (ramping from −40° C. to −20° C. in the range of 0.5 h-1.5 h. Final freezing at −50° C. for 3 h to 4h.

iii. Sublimation of ice at −42° C. for a maximum of 15 h followed by a further sublimation at −40° C. for another 15 h to 90 h or at a temperature range of −38° C. to −35° C. for a maximum of 55 h under the vacuum conditions of 50 mTorr.

iv. Secondary drying at 20° C. to 25° C. range for 10 h to 15 h at 50 mTorr vacuum.

Resulting freeze drying samples are evaluated for initial potency (t=0) compared to non-freeze dried aqueous liquid 'feed' samples. Some of the freeze dried samples are incubated at 37° C.±2° C. with Relative Humidity (RH) of 75%±5% storage conditions for different time points and compared with samples stored at 2° C. to 8° C. storage conditions as shown in Table 4. Among all the formulations evaluated, 1000, 1004, 1005, 1011 & 1013 retained G1 potency is measured up to 4 weeks when stored at 37° C.±2° C. (RH 75%±5%). Among the formulations with Dextran as a bulking agent, 1030 retained G1 potency up to 4 weeks at 37° C.±2° C. (RH 75%±5%). However this formulation is observed to be unsuitable for optimal freeze drying based on DTA and the impedance analysis data.

(d) All formulations are also evaluated for the moisture content using Karl Fischer method. The formulations 1005, 1011 & 1013 showed very high moisture content in repeated trials as shown in Table 5. The formulations 1000 and 1004 showed elegant cake appearance as well as low moisture content as compared to the other three formulations. These formulations are also observed to be better in terms of retaining the rotavirus potency at 37° C.±2° C. (RH 75%±5%). The formulation 1002 although showed a lower moisture content but lost potency at 37° C.±2° C. (RH 75%±5%) during $2^{nd}$ week of storage.

The freeze dried formulations 1000 and 1004 that yielded elegant cakes with low moisture content. It is observed that the process and the stability loss for G1 serotype did not exceed $\log_{10}$=[0.5] during storage at 37° C.±2° C. (RH 75%±5%) are used as exemplified formulations in subsequent studies.

Additionally, from statistical treatment of potency and DTA data of DoE formulations an optimized combination of stabilizer emerged comprising of 25 mM HEPES, Sucrose: PVP ratio of 1.6:6.4 (g %: g %), 25 mM NaCl, 50 mM L-Arginine, 100 mM Glycine and 2 mM CaCl2.2H2O.

TABLE 3

Composition of best performing formulations with respect to potency identified during Freeze-Thaw-Stability experiments

| Formulat$^n$ ID | HEPES (mM) | NaCl (mM) | Sucrose (%) | PVP-K25 (%) | L-Arginine (mM) | Glycine (mM) | $CaCl_2$•$2H_2O$ (mM) | $ZnCl_2$ (mM) | Tween-20 (%) | Dextran (%) |
|---|---|---|---|---|---|---|---|---|---|---|
| 1000 | 10 | 50 | 1.2 | 4.8 | 100 | 0 | 2 | 0 | 0.02 | 0 |
| 1001 | 25 | 25 | 3 | 3 | 50 | 50 | 1 | 1 | 0.01 | 0 |
| 1002 | 10 | 0 | 1.2 | 4.8 | 10 | 0 | 0 | 0 | 0 | 0 |
| 1004 | 50 | 0 | 4 | 2 | 100 | 0 | 2 | 0 | 0 | 0 |
| 1005 | 50 | 50 | 1.2 | 4.8 | 10 | 100 | 2 | 0 | 0 | 0 |
| 1011 | 50 | 50 | 4 | 2 | 100 | 100 | 2 | 2 | 0.02 | 0 |
| 1013 | 10 | 50 | 4 | 2 | 100 | 100 | 0 | 0 | 0 | 0 |
| 1030 | 50 | 50 | 4 | 2 | 100 | 100 | 2 | 2 | 0.02 | 2 |

TABLE 4

Stability log loss of freeze dried monovalent formulations containing G1 serotype when exposed at 37° C. (RH 75% ± 5%) for 4 weeks

| Storage condition | 1000 | 1001 | 1002 | 1004 | 1005 | 1011 | 1013 | 1030 |
|---|---|---|---|---|---|---|---|---|
| 37° C. | 0 | 0.12 | 0.70 | 0.19 | 0 | 0 | 0 | 0 |
| 2-8° C. | 0 | 0.21 | 0.30 | 0 | 0 | 0 | 0.26 | 0 |

TABLE 5

Percent moisture content of selected freeze dried formulations evaluated using Karl Fischer's method

| Formulation | 1000 | 1001 | 1002 | 1004 | 1005 | 1011 | 1013 | 1030 |
|---|---|---|---|---|---|---|---|---|
| Moisture content | 0.75 | 1.37 | 0.82 | 0.84 | 4.98 | 4.84 | 4.03 | 1.19 |

Study 2: Selection of Optimal Buffer and Bulking Agent Combination.

The optimized combination (1057 as shown in Table 6 of stabilizers obtained by statistical treatment of potency and DTA data of DoE formulations in Example 1, Study 1; is further tested for optimizing buffer and bulking agents by evaluating for potency changes. Three bulking agents and buffer combinations are used to identify best performing combination resulting in various formulations as shown in Table 6. The compositions are formulated with G1 and G3 strains. The target concentration is each strain is 7.0 log/mL. The formulation 1065H is same as 1065 with annealing step added in freeze drying cycle. The freeze drying cycle is 50 h duration characterized by:

i. Precooling the freeze dryer shelf to −45° C. prior to vial loading.

ii. Freezing step for 1.5 h followed by holding at the same temperature for 30 minutes.

iii. Primary drying by raising the temperature to −2.0° C. followed by a ramp down to −30° C. within 2 h. Further ramping down the temperature to −36° C. within 3 h and finally to −38° C. in 5 h and holding the product at this temperature for 23 h followed by a further ramping up to −10° C. in 4 h. The vacuum maintained during all the primary drying steps is 0.080 mBar.

iv. Secondary drying by increasing the temperature up to 25° C. within 30 min and holding the product at same temperature for 8 h under zero vacuum.

TABLE 6

Composition of optimized formulations used to determine the effect of buffer and bulking agent combination on process and longitudinal stability of representative rotavirus serotypes

| Formulation | Buffer (mM) | NaCl (mM) | Sucrose: Bulking agent (g %:g %) | L-Arginine (mM) | Glycine (mM) | $CaCl_2 \cdot 2H_2O$ (mM) | $ZnCl_2$ (mM) | Tween (%) |
|---|---|---|---|---|---|---|---|---|
| 1057 | 25 (HEPES) | 25 | 1.6:6.4 PVP K-40 | 50 | 100 | 2 | 0 | 0 |
| 1060 | 25 (Tris) | 25 | 1.6:6.4 PVP K-40 | 50 | 100 | 2 | 0 | 0 |
| 1063 | 25 (Phosphate) | 25 | 1.6:6.4 PVP K-40 | 50 | 100 | 2 | 0 | 0 |
| 1065 | 25 (Phosphate) | 25 | 1.6:6.4 Mannitol | 50 | 100 | 2 | 0 | 0 |
| 1063T | 25 (Phosphate) | 25 | 1.6:6.4 Mannitol | 50 | 100 | 2 | 0 | 0.01 |
| 1065H | 25 (Phosphate) | 25 | 1.6:6.4 Mannitol | 50 | 100 | 2 | 0 | 0 |

In some compositions; 1065H, an additional annealing step was added resulting in a 58 h cycle characterized by:

i. Precooling the freeze dryer shelf to −45° C. prior to vial loading.

ii. Freezing step for 1.5 h followed by holding at the same temperature for 30 minutes.

iii. Annealing step by increasing the temperature from −45° C. to −15° C. within 5 minutes and then holding at the same temperature for 2 h followed by refreezing the product to −45° C. for 1 h.

iv. Primary drying by raising the temperature to −7.0° C. within 15 minutes followed by a further ramp down to −27° C. within 2 h. The temperature is further decreased to −33° C. within 3 h and finally to −35° C. in 5 h. The product is held at this temperature for 30 h. The vacuum maintained during all the primary drying steps is 0.080 mBar. This step was followed by a further ramp up to −10° C. in 4 h under zero vacuum.

v. Secondary drying by raising the temperature to 25° C. within 30 min and holding the product at the same temperature for 8 h under zero vacuum.

The freeze dried formulations are stored at 37° C.±2° C. (RH 75%±5%) and 2° C.-8° C. for four weeks. The log loss values are analyzed by M-QPA as shown in Table 7. Compositions with PVP as a bulking agent in combination with HEPES as buffering agent resulted in best retention of potency for representative rotavirus serotypes G1 and G3.

The best performing formulations in terms of potency retention, 1057 and 1063, are further evaluated for their ability to support the potency of five (G1, G2, G3, G4 and P1) human bovine rotavirus serotypes under the storage conditions of 2° C.-8° C. and 37° C.±2° C. (RH 75%±5%). It is found that HEPES containing formulation, 1057, best supported potency of all five serotypes at high temperatures as compared to Phosphate containing 1063 as shown in Table 8. Composition involving phosphate buffer also resulted in precipitating $Ca^{+2}$ ions in formulation indicating essential role of $Ca^{+2}$ in longitudinal stability.

Study 4: Longitudinal studies and Reproducibility for Exemplified Lead Formulations 1000 and 1004 in Vials.

The two exemplified formulations from Study 1, 1000 and 1004 are tested for longitudinal stability at 37° C. and 2° C. to 8° C. storage conditions, incorporating all the five (G1, G2, G3, G4 and P1) human-bovine rotavirus strains as shown in Table 9. The formulation's compositions, storage conditions and potency analysis are similar as described in Study 1. The initial potency for each serotype is 7.0 log /mL A 99 h cycle is used for freeze drying these formulations as described below:

TABLE 7

Effect of different Buffer and Bulking Agent combination on the stability loss of G1 and G3 strains

| Storage condition | 1057 | | 1060 | | 1063 | | 1063T | | 1065 | | 1065H | |
|---|---|---|---|---|---|---|---|---|---|---|---|---|
| | G1 | G3 | G1 | G3 | G1 | G3 | G1 | G3 | G1 | G3 | G1 | G3 |
| 37° C. | 0.09 | 0.09 | 0.34 | 0.51 | 0.10 | 0.16 | 0.16 | 0.10 | 0.25 | 0.68 | 0.83 | 1.33 |
| 2-8° C. | 0 | 0 | 0 | 0.16 | 0 | 0 | 0 | 0 | 0 | 0 | 0 | 0.07 |

TABLE 8

Stability loss of pentavalent rotavirus formulations 1057 and 1063 with different buffering components for 4 weeks

| Formulation | Temperature condition | G1 | G2 | G3 | G4 | P1 |
|---|---|---|---|---|---|---|
| 1057 | 37° C. | 0.27 | 0 | 0.20 | 0 | 0.04 |
| | 2-8° C. | 0.17 | 0 | 0.01 | 0 | 0 |
| 1063 | 37° C. | 0.53 | 0.68 | 0.14 | 0.62 | 0.45 |
| | 2-8° C. | 0.16 | 0.17 | 0 | 0.24 | 0.03 |

Study 3: Formulation of Reconstitution Buffer to Provide Acid Neutralization Capacity (ANC) to Vaccine.

The exemplified lead formulations from above studies did not exhibit adequate ANC of by themselves. Therefore a reconstitution buffer is prepared to provide the desired ANC sufficient to protect the live virus from gastric acid. Each 2.0 mL of reconstitution buffer is formulated with 400 mg of sucrose, 29.8 mg of sodium dihydrogen phosphate monohydrate and 127 mg of trisodium citrate dihydrate in water q.s to 2.0 mL.

The ANC value is determined using method described by United States Pharmacopeia 34 NF 29. The experiment is conducted in triplicate. The results are expressed in terms of mEq per dose. All the above lead formulations when dissolved in the reconstitution buffer are observed to yield an ANC value of 0.8 mEq/ dose of 2.0 mL.

i. The pre freeze drying liquid is precooled to 10° C. to 12° C. and loaded into the freeze dryer followed by a freeze drying cycle.

ii. The temperature is decreased from 4° C. to −40° C. in 60 minutes. The freezing step is carried out at −40° C. for 3 h followed by annealing at −20° C. for another 2 h. The annealing temperature is obtained within 20 minutes. Temperature is further decreased to −50° C. within 60 minutes followed by holding the vials at the same temperature for 4 h.

iii. The primary drying is carried at −42° C. for 10 h followed by a further sublimation at −40° C. for 15 h and then at a temperature of −37° C. for 45 h under the vacuum conditions of 50 mTorr. The temperature is ramped up slowly from −42° C. to −40° C. and −40° C. to −37° C. in 15 minutes.

iv. Secondary drying was conducted at 20° C. for 15 h at 50 mTorr vacuum.

The aqueous liquid feed solid contents are in the range of 10.00 g/100mL to 25.00 g/100 mL for optimal drying, yield and or cake appearance.

Process loss is calculated as a difference of potency between samples obtained before and after freeze drying. Stability log loss per 30 days at 37° C.±2° C. with % RH 75%±5% is calculated by linear regression of potency data of samples incubated at 37° C.±2° C. and % RH 75%±5% for at least 30 days with 7 day sampling intervals.

TABLE 9

Summary of the process loss, stability loss and the cumulative loss of pentavalent composition in 1000 and 1004 formulations. n = 1, 2 and 3 are the three independent manufacturing batches.

| Stability data obtained | Process loss | | | | | Stability loss (log10) per 30 days at 37° C. | | | | | Cumulative loss (process loss + Stability loss at 37° C. for 30 days) | | | | |
|---|---|---|---|---|---|---|---|---|---|---|---|---|---|---|---|
| Formulation | G1 | G2 | G3 | G4 | P1 | G1 | G2 | G3 | G4 | P1 | G1 | G2 | G3 | G4 | P1 |
| 1000 (n = 1) | 0.18 | 0.0 | 0.03 | 0.0 | 0.11 | 0.02 | 0.10 | 0.06 | 0.01 | 0.28 | 0.20 | 0.10 | 0.09 | 0.01 | 0.39 |
| 1000 (n = 2) | 0.01 | 0.0 | 0.01 | 0.0 | 0.0 | 0.02 | 0.04 | 0.11 | 0.0 | 0.19 | 0.03 | 0.04 | 0.12 | 0.0 | 0.19 |
| 1000 (n = 3) | 0.15 | 0.07 | 0.0 | 0.0 | 0.09 | 0.12 | 0.17 | 0.06 | 0.12 | 0.21 | 0.26 | 0.24 | 0.06 | 0.12 | 0.30 |
| 1004 (n = 1) | 0.01 | 0.0 | 0.09 | 0.01 | 0.0 | 0.09 | 0.0 | 0.16 | 0.11 | 0.12 | 0.10 | 0.0 | 0.25 | 0.12 | 0.12 |

TABLE 9-continued

Summary of the process loss, stability loss and the cumulative loss of pentavalent composition in 1000 and 1004 formulations. n = 1, 2 and 3 are the three independent manufacturing batches.

| Stability data obtained | Process loss | | | | | Stability loss (log10) per 30 days at 37° C. | | | | | Cumulative loss (process loss + Stability loss at 37° C. for 30 days) | | | | |
|---|---|---|---|---|---|---|---|---|---|---|---|---|---|---|---|
| Formulation | G1 | G2 | G3 | G4 | P1 | G1 | G2 | G3 | G4 | P1 | G1 | G2 | G3 | G4 | P1 |
| 1004 (n = 2) | 0.0 | 0.0 | 0.0 | 0.0 | 0.12 | 0.0 | 0.0 | 0.06 | 0.0 | 0.0 | 0.0 | 0.0 | 0.06 | 0.0 | 0.12 |
| 1004 (n = 3) | 0.03 | 0.0 | 0.0 | 0.03 | 0.14 | 0.05 | 0.06 | 0.07 | 0.0 | 0.03 | 0.08 | 0.06 | 0.07 | 0.03 | 0.17 |

Study 5: Longitudinal Thermostabilty and Reproducibility for Formulation 1004 in Vials.

The exemplified formulation 1004 is tested for longitudinal stability and process reproducibility under the storage conditions of 37° C.±2° C. (RH 75%±5%), 45° C.±2° C. (RH 75%±5%) and 2° C.-8° C. The formulation is incorporated with all the five strains at the log concentrations per dose/ml as G1: 6.81; G2: 6.92; G3: 6.91; G4: 6.78 and P1: 6.83 (1× concentrations). A 63 h freeze drying cycle is developed and optimized for preparation of this formulation and is found to support freeze drying of full load in the freeze dryer (>680 vials per batch). The details of the freeze drying cycle are mentioned below:

a. The pre freeze drying liquid is precooled to 10° C. to 12° C. and loaded into the freeze dryer followed by a freeze drying cycle.

b. The temperature is ramped down from 4° C. to −40° C. within 60 minutes and the freezing step is carried out at −40° C. for 2 h followed by annealing for another 2 h at −20° C. The annealing temperature is brought within 60 minutes. A further ramp down is carried out up to −40° C. within 60 minutes. The final freezing is carried out at −40° C. for 1.5 h.

c. The temperature is brought up to −33° C. within 4 h and primary drying is carried out at −33° C. for 33 h followed by a temperature ramp to −10° C. within 6 h and then to 0° C. and 25° C. within 3 h each. A 50 mTorr of vacuum is maintained during the primary drying steps.

d. The secondary drying is carried out at 25° C. for 5 h at 0 mTorr.

The final residual moisture content of all the three independent manufacturing batches is below 2.0%. The formulation retained its potency at 37° C.±2° C. (RH 75%±5%), 45° C.±2° C. (RH 75%±5%) and 2° C.-8° C. for at least 12 weeks. Process loss is calculated as a difference of potency between samples before and after freeze drying.

Stability loss (log loss) is calculated by linear regression of potency data of samples incubated under different storage conditions. The values mentioned in the brackets represent the potency log loss values at 45° C.±2° C. (RH 75%±5%) for 12 weeks as shown in Table 10.

TABLE 10

Summary of the log process loss, log stability loss and the log cumulative loss of pentavalent composition in 1004 formulation (37° C./2-8° C./45° C.). N = 1, 2 and 3 are three independent manufacturing batches

| | Rotavirus Serotype | N = 1 (% MC: 1.22) | N = 2 (% MC: 1.10) | N = 3 (% MC: 0.68) |
|---|---|---|---|---|
| Process Loss | G1 | 0.0 | 0.0 | 0.04 |
| | G2 | 0.03 | 0.0 | 0.02 |
| | G3 | 0.01 | 0.0 | 0.11 |
| | G4 | 0.0 | 0.0 | 0.06 |
| | P1 | 0.16 | 0.11 | 0.12 |
| Stability Loss | G1 | 0.11/0.11/0.12 | 0.06/0/0.38 | 0/0/0.20 |
| | G2 | 0.06/0.05/0.19 | 0.12/0.03/0.25 | 0.09/0/0.29 |
| | G3 | 0/0/0.08 | 0.02/0/0.14 | 0.08/0.03/0.29 |
| | G4 | 0.04/0.02/0.27 | 0 | 0.17/0.04/0.24 |
| | P1 | 0.09/0.08/0.29 | 0.14/0/0.39 | 0.33/0.13/0.23 |
| Cumulative loss | G1 | 0.11/0.11/0.12 | 0.06/0/0.38 | 0.04/0.04/0.24 |
| | G2 | 0.09/0.08/0.22 | 0.12/0.03/0.25 | 0.11/0.02/0.31 |
| | G3 | 0.01/0.01/0.09 | 0.02/0/0.14 | 0.19/0.14/0.40 |
| | G4 | 0.04/0.02/0.27 | 0 | 0.23/0.10/0.30 |
| | P1 | 0.25/0.24/0.45 | 0.25/0/0.5 | 0.45/0.25/0.35 |

Example 2

Designing Scalable and Reproducible Freeze Drying Process for Thermostabilization of Rotavirus Vaccine Study 1: Optimization of Formulation This formulation 1004 exhibited suboptimal cake properties at pilot scales with higher titres (>2000 doses) and is further optimized by varying bulking agent concentrations and the sugar: bulking agent ratios so as to increase the solid contents of the formulation generating three variants of 1004 as shown in Table 11. These modified formulations supported a freeze drying cycle of 54 h duration involving following steps;

i. precooling a pre freeze-drying liquid to 10° C. to 12° C. and loading into the freeze dryer ii. Freezing the pre freeze-drying liquid at −35° C. (temperature ramp of 4° C. to −35° C.: 2 h) for 1 h and at −45° C. for 1.5 h (temperature ramp of −35° C. to −45° C.: 0.5 h) followed by annealing at −20° C. for another 2 h (temperature ramp of −45° C. to −20° C.: 1 h). Final freezing at −40° C. for 1.5 h (temperature ramp of −20° C. to −40° C.: 0.5 h)

iii. Primary drying at −32° C. for 1 h and at −28° C. for 24 h (temperature ramp from −40° C. to −32° C. and from −32° C. to −28° C.: 1 h each) under 50 mTorr vacuum. Temperature ramp up from −28° C. to 0° C.:

10 h) followed by a secondary drying at 25° C. for 5 h under 0 mTorr vacuum (Temperature ramp of 0° C. to 25° C.: 2 h).

The final residual moisture content of all the above three formulations is below 1.0% (<1.0%) with elegant cakes however 1004b and 1004c were better in terms of cake appearance throughout the shelf-life. Each formulation is freeze dried in vials with all five (G1, G2, G3, G4 and P1) human-bovine rotavirus serotypes using above cycle and are evaluated for potency changes when stored at 37° C.±2° C. (RH 75%±5%), and 2° C. to 8° C. The process loss is calculated as a difference of potency between samples before and after freeze drying. The stability loss (log loss) per 30 days at 2° C. to 8° C. and at 37° C. ±2° C. (RH 75%±5%) is calculated by linear regression of potency data of samples incubated under this storage condition. The initial log potency values per ml of liquid feed are G1: 6.81; G2: 6.92; G3: 6.91; G4: 6.78 and P1: 6.83. All modified formulations showed elegant cakes and show potency exhibited process, stability and cumulative process loss that did not exceed $Log_{10}$=0.5 for 30 days as shown in Table 12.

TABLE 11

Composition of optimized formulations used to determine the effect of bulking agent concentrations and the sugar:bulking agent ratios

| Formulation | HEPES (mM) | Sucrose:PVP K-25 (gm %:gm %) | L-Arginine (mM) | $CaCl_2 \cdot 2H_2O$ (mM) |
| --- | --- | --- | --- | --- |
| 1004a | 50 | 4.0:4.0 | 100 | 2 |
| 1004b | 50 | 4.0:6.0 | 100 | 2 |
| 1004c | 50 | 6.0:4.0 | 100 | 2 |

TABLE 12

Summary of the process loss, stability loss and the cumulative loss of pentavalent composition in 1004a, 1004b and 1004c formulations.

| | Process loss | | | | | | Stability log loss per 30 | | | | | Cumulative log loss per 30 | | | | |
| --- | --- | --- | --- | --- | --- | --- | --- | --- | --- | --- | --- | --- | --- | --- | --- | --- |
| Formul$^n$ | G1 | G2 | G3 | G4 | P1 | | G1 | G2 | G3 | G4 | P1 | G1 | G2 | G3 | G4 | P1 |
| 1004a | 0.18 | 0.06 | 0 | 0.03 | 0 | 37° C. | 0.10 | 0 | 0 | 0 | 0 | 0.28 | 0.06 | 0 | 0 | 0 |
| | | | | | | 2-8° C. | 0.01 | 0 | 0 | 0 | 0.02 | 0.19 | 0.06 | 0 | 0 | 0 |
| 1004b | 0.01 | 0.11 | 0.16 | 0 | 0.08 | 37° C. | 0.20 | 0 | 0.03 | 0.14 | 0.07 | 0.21 | 0.11 | 0.19 | 0.14 | 0.15 |
| | | | | | | 2-8° C. | 0.17 | 0 | 0.03 | 0.05 | 0.04 | 0.18 | 0.11 | 0.19 | 0.05 | 0.12 |
| 1004c | 0 | 0.14 | 0 | 0.06 | 0 | 37° C. | 0.23 | 0.02 | 0.06 | 0.06 | 0.08 | 0.23 | 0.16 | 0.06 | 0.12 | 0.08 |
| | | | | | | 2-8° C. | 0.15 | 0 | 0 | 0.02 | 0.02 | 0.15 | 0.14 | 0 | 0.09 | 0.02 |

Study 2: Longitudinal Thermostability and Reproducibility for Formulation 1004c in vials.

The exemplified formulation 1004c is tested for longitudinal stability and process reproducibility at clinically relevant concentrations of rotavirus, under the storage conditions of 37° C.±2° C. (RH 75%±5%) and 2° C. to 8° C. for 8 weeks. The formulation is incorporated with all the five strains at the log concentrations per dose per ml as G1: 6.81; G2: 6.92; G3: 6.91; G4: 6.78 and P1: 6.83 (1× concentrations). A 54 h freeze drying cycle as mentioned in Example 2 of Study 1, is used for preparation of this formulation and is found to support freeze drying of full load in the freeze dryer (>680 vials per batch). The total solid content is 13 g/100 ml in aqueous liquid feed.

Process loss is calculated for three independent manufacturing batches (N=1, 2, 3), as a difference of potency between samples before and after freeze drying.

Stability loss (log loss) at 37° C.±2° C. with %RH 75%±5% is calculated by linear regression of potency data of samples incubated at 37° C.±2° C. and % RH 75%±5% as shown in Table 13. The moisture content of all the three manufacturing batches are below 2.0% (<2.0%).

TABLE 13

Summary of the process loss, stability loss and the cumulative loss of pentavalent composition in 1004c formulations in three independent manufacturing batches

| Formulat[n] | Process loss | | | | | | Stability log loss per 8 | | | | | Cumulative log loss per 8 | | | | |
|---|---|---|---|---|---|---|---|---|---|---|---|---|---|---|---|---|
| | G1 | G2 | G3 | G4 | P1 | | G1 | G2 | G3 | G4 | P1 | G1 | G2 | G3 | G4 | P1 |
| N = 1 | 0 | 0.14 | 0 | 0.06 | 0 | 37° C. | 0.43 | 0.04 | 0.11 | 0.11 | 0.14 | 0.43 | 0.18 | 0.11 | 0.17 | 0.14 |
| | | | | | | 2-8° C. | 0.29 | 0 | 0 | 0.04 | 0.04 | 0.29 | 0 | 0 | 0.10 | 0.04 |
| N = 2 | 0.11 | 0.12 | 0.12 | 0.15 | 0.12 | 37° C. | 0.11 | 0.21 | 0.12 | 0.02 | 0.16 | 0.22 | 0.33 | 0.24 | 0.18 | 0.28 |
| | | | | | | 2-8° C. | 0.03 | 0.06 | 0 | 0 | 0 | 0.14 | 0.17 | 0 | 0 | 0 |
| N = 3 | 0.10 | 0.07 | 0.07 | 0.12 | 0.13 | 37° C. | 0.21 | 0.18 | 0.16 | 0.10 | 0.13 | 0.31 | 0.25 | 0.23 | 0.22 | 0.27 |
| | | | | | | 2-8° C. | 0.07 | 0.17 | 0.04 | 0.08 | 0.03 | 0.17 | 0.24 | 0.11 | 0.21 | 0.17 |

Study 3: Titer scale up, Longitudinal studies and Reproducibility for 1004c formulation in vials.

The composition for the formulation is same as that used in Example 2 of Study 1 except that the initial human-bovine rotavirus serotype concentrations is increased 5 times (5×) with the log values per ml per 5 doses as G1: 7.51; G2: 7.62; G3: 7.61; G4: 7.47; P1: 7.52 in vials. The total solid content is 13 g/100 ml in aqueous liquid feed for all the three independent manufacturing batches N=1, 2 and 3. The solution pH is adjusted to 6.10±0.1. The 54 h freeze drying cycle (similar to Study 1 of Example 2) is used for preparation of this formulation in Type-I glass vials with 3 mL capacity.

Figure 2:
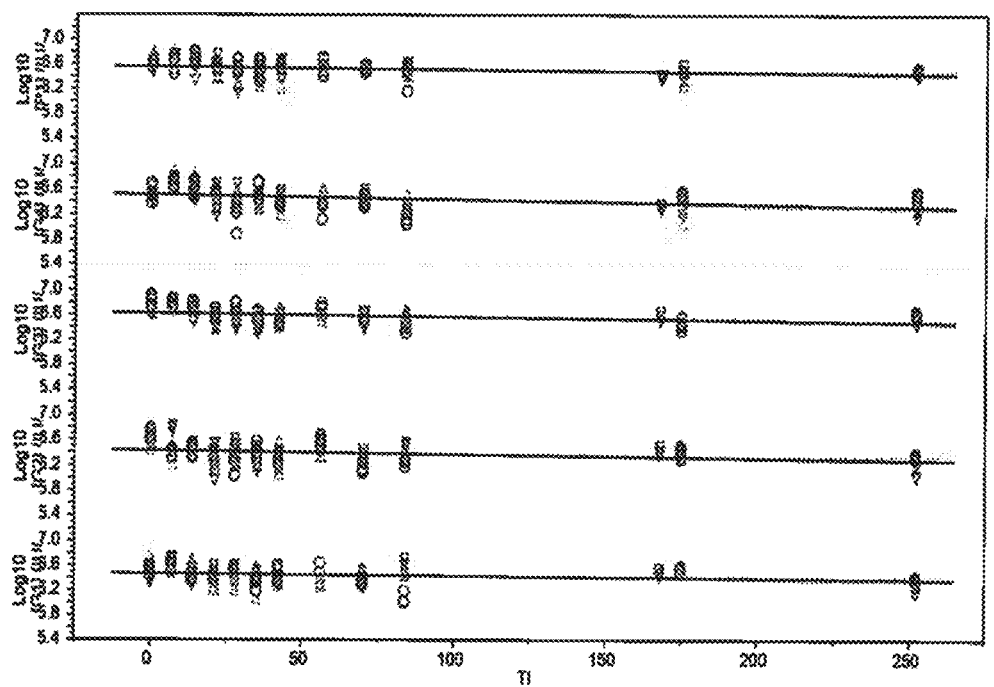
FIG. 2: Stability data of freeze dried formulation 1004c in vials containing five human bovine serotypes (G1, G2, G3, G4 and P1) for N=1 (○), N=2 (Δ) and N=3 (□) at 37° C. storage conditions.
Figure 3:
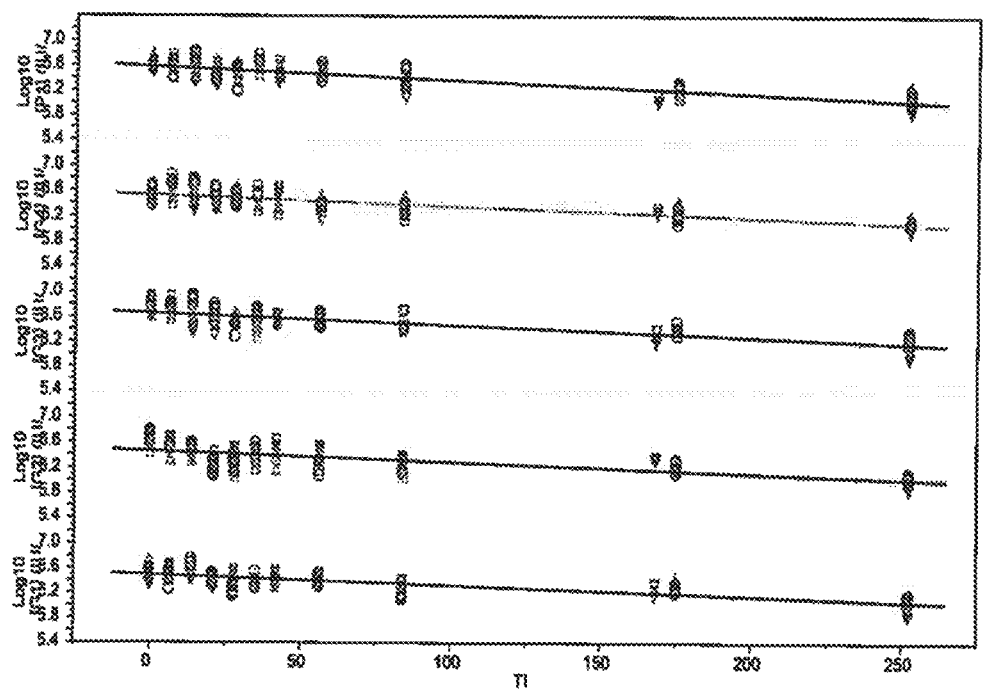
FIG. 3: Stability data of freeze dried formulation 1004c in vials containing five human bovine serotypes (G1, G2, G3, G4 and P1) for N=1 (○), N=2 (Δ) and N=3 (□) at 45° C. storage conditions.

A negligible process loss is observed when compared to the pre- freeze drying liquid control. The longitudinal studies are conducted under the storage conditions of 2° C.-8° C., 37° C.±2° C. (RH 75%±5%) and 45° C.±2° C. (RH 75%±5%). The data is depicted in FIG. 1, FIG. 2 and FIG. 3 respectively. Based on the linear regression of this data, it is observed that the freeze dried rotavirus formulation is stable at all these storage conditions for almost 252 days (9 months). Slope values for the samples stored at 2° C. to 8° C. showed no loss. Arrhenius kinetics simulations of the data indicated that expected time period for stability, as indicated by $Log_{10}$=0.5 potency loss for any of the five serotypes within this formulation, at 37° C.±2° C. (RH 75%±5%) can be 23 months. Similar treatment of the data showed that at 45° C.±2° C. (RH 75%±5%) storage conditions, a loss of $Log_{10}$=0.5 in the potency is observed within 9 months and is confirmed in real time.

Study 4: Bulk freeze drying of exemplified formulation 1004c in trays

The formulation 1004c is freeze dried in Stainless Steel (SS) trays at 5× concentrations of rotavirus. A 380 mL of pre freeze drying liquid is added into SS tray thus giving the liquid height same as that obtained in vials in Study 2 and 3 of Example2. Three independent manufacturing batches N=1, 2 and 3 were prepared.

However for optimal cake properties and moisture content the bulk freeze drying in trays required the freeze drying cycle of 70 h duration. This freeze drying cycle involve following steps;
  i. precooling a pre freeze-drying liquid to 10° C. to 12° C. and loading into the freeze dryer
  ii. freezing pre freeze-drying liquid at −35° C. for 1 h (Temperature ramp of 4° C. to −35° C.: 2 h) and at −45° C. for 1.5 h (Temperature ramp of −35° C. to −45° C.: 0.5 h) followed by annealing at −20° C. for another 2 h (Temperature ramp of −45° C. to 20° C.: 1 h). Final freezing at −40° C. for 1.5 h (Temperature ramp of −20° C. to −40° C.: 0.5 h)
  iii. Primary drying is carried at −32° C. for 1 h and at −28° C. for 34 h (Temperature ramp of −40° C. to −32° C. and −32° C. to −28° C.: 1 h each) under a vacuum of 50 mTorr.
  iv. Secondary drying of cake at 25° C. for 5 h under 0 mTorr vacuum conditions. (Temperature ramp of −28° C. to 0° C.: 15.5 h and from 0° C. to 25° C.: 2 h)

The final residual moisture content of all the above mentioned three independent manufacturing batches is below 3% (<3.0%) thereby preventing degradation pathways in rotavirus serotypes associated with the presence of excess water. An elegant cake is observed in trays with no collapse which is confirmed visually.

Study 5: Processing of Bulk Freeze Dried Cake to Obtain Free Flowing Powders.

In order to obtain a powder suitable for filling in the final packaging container/closure the bulk freeze dried pentavalent rotavirus vaccine cake is milled using Ball milling in 250 mL or 2.0 L stainless steel gas tight vessel in a Turbula Mixer (Willy A. Bachofen AG, Switzerland. Type T2F No. 131266). The vaccine cake and the steel balls are added to obtain a weight ratio of 1:10. The turbula mixer is operated for 105 sec at a speed of 72 rpm. Milled cake is checked visually for completion and further milling of 30 seconds is performed as required. All sample preparation steps prior to enclosing in container is carried out under low RH conditions (<5%) in a nitrogen purged glove box.

Micronized pentavalent rotavirus freeze dried vaccine is blended with Maltodextrin DE 6-8 (Glucidex 6D) as a blending agent using a 250 mL or 2.0 L stainless steel gas tight vessel in Turbula Mixer (Willy A. Bachofen AG, Switzerland. Type T2F No. 131266). The blending is conducted at 23 rpm for 15 minutes followed by a further 2-3 minutes at 32 rpm. The milled and blended formulations are characterized for Particle size distribution, dissolution time, pH after reconstitution, residual moisture content and the glass transition temperature ($T_g$). The $T_g$ is obtained in a step-scan DSC with a series of micro-steps with temperature increase at a particular ramp rate followed by an isothermal period.

Following observations are made on the blended powder;

i. The particle sizes characterized by $D_{50}$ and $D_{90}$ of the milled powder, reported as mean volume diameter, are observed to be 85 and 291 μm respectively whereas the blending agent showed particle sizes of 91 and 270 μm respectively.
ii. Both the milled freeze dried powder and the blending agent showed irregular shaped particles when observed microscopically.
iii. Milled samples exhibited residual moisture in a range of 2.0% to 2.5% whereas the final blended powders showed low moisture content of 1.0% to 1.5%.

iv. The pH of pre-freeze drying liquid is 6.10±0.1. The milled and blended freeze dried pentavalent rotavirus vaccine powder is reconstituted with the reconstitution buffer and the reconstituted vaccine exhibited an Acid Neutralization Capacity (ANC) of 0.80 mEq/dose of 2 ml. The pH of vaccine after reconstitution was observed to be 6.10±0.1.

v. The Modulated Differential Scanning calorimetry (MDSC) showed a $T_g$ as a sharp transition with an onset as a reversing event at 48° C.±1° C. for the milled dried powder for three independent tray dried manufacturing batches.

each are dispensed into eppendorfs tubes with 1.5 mL capacity and are incubated at 2° C.-8° C., 25° C., 37° C. and −70° C. storage conditions in the incubators. The samples are collected at 0 h, 8 h, 11 h, 35 h and 48 h time intervals and are evaluated for the potency. The potency of rotavirus remaining at above conditions is determined by comparing the IU/dose of the freeze dried vaccine incubated under above mentioned conditions with samples that are incubated at −70° C.

The data obtained from these studies show potency is retained for 8-11 hours 25° C. for all the five strains as shown in Table 14. At 2° C. to −8° C. and −70° C. storage conditions, the reduction in the potencies is negligible.

TABLE 14

$Log_{10}$ potency values of five rotavirus serotypes when reconstituted with reconstitution buffer and incubated under different temperatures

| | Rotavirus strains | | | | | | | | | | | | | |
|---|---|---|---|---|---|---|---|---|---|---|---|---|---|---|
| | G1 | | | G2 | | | G3 | | | G4 | | | P1 | | |
| Time | 25° C. | 2-8° C. | −70° C. | 25° C. | 2-8° C. | −70° C. | 25° C. | 2-8° C. | −70° C. | 25° C. | 2-8° C. | −70° C. | 25° C. | 2-8° C. | −70° C. |
| 0 h | 6.85 | 6.85 | 6.85 | 6.95 | 6.95 | 6.95 | 7.02 | 7.02 | 7.02 | 6.73 | 6.73 | 6.73 | 6.76 | 6.76 | 6.76 |
| 8 h | 6.80 | 6.80 | 6.90 | 7.02 | 7.03 | 7.06 | 6.99 | 7.06 | 7.03 | 6.72 | 6.78 | 6.77 | 6.72 | 6.76 | 6.70 |
| 11 h | 6.80 | 6.81 | 6.85 | 6.99 | 7.00 | 7.03 | 6.90 | 6.95 | 6.99 | 6.71 | 6.81 | 6.76 | 6.69 | 6.72 | 6.71 |
| 35 h | 6.74 | 6.81 | 6.82 | 6.94 | 6.95 | 7.00 | 6.73 | 6.84 | 6.95 | 6.67 | 6.64 | 6.72 | 6.66 | 6.68 | 6.67 |
| 48 h | 6.74 | 6.74 | 6.82 | 6.92 | 6.94 | 6.98 | 6.64 | 6.95 | 7.01 | 6.56 | 6.68 | 6.73 | 6.66 | 6.68 | 6.69 | vi. The dissolution time for the single dose pentavalent rotavirus vaccine blended powder (130 mg) in 2.0 mL of reconstitution buffer maintained at 23.0° C.±1.0° C. is observed to be 60±5.0 seconds with manual gentle shaking of vial. At buffer temperatures maintained at 2° C. to 8° C., it took almost 2 minutes to dissolve the pentavalent rotavirus vaccine completely with gentle manual shaking.

Study 6: Longitudinal Stability Studies and Reproducibility Studies for Milled and Blended Freeze Dried Lead Formulation.

Figure 4:
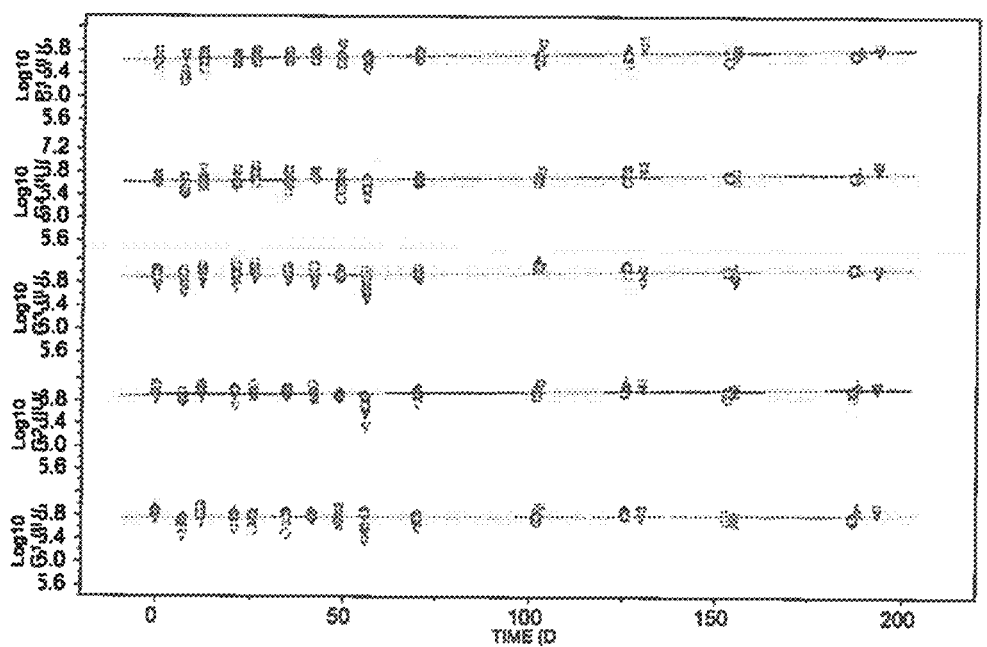
FIG. 4: Stability data of freeze dried, milled and blended formulation 1004c containing five human bovine serotypes (G1, G2, G3, G4 and P1) for N=1 (○), N=2 (Δ) and N=3 (□) at 2° C. to 8° C. storage conditions.
Figure 5:
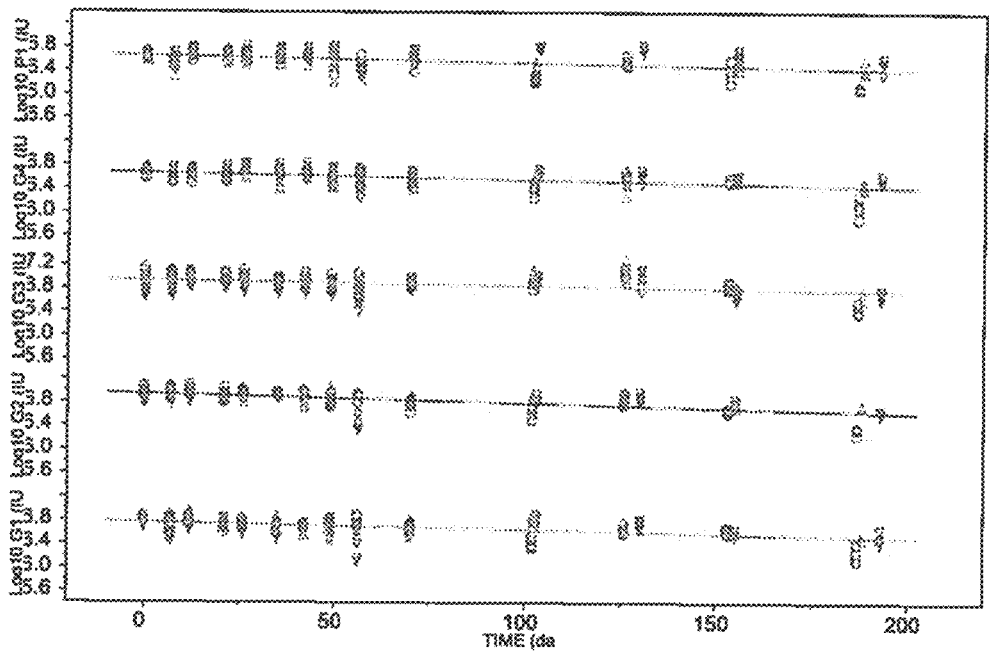
FIG. 5: Stability data of freeze dried, milled and blended formulation 1004c containing five human bovine serotypes (G1, G2, G3, G4 and P1) for N=1 (○), N=2 (Δ) and N=3 (□) at 37° C. storage conditions.
Figure 6:
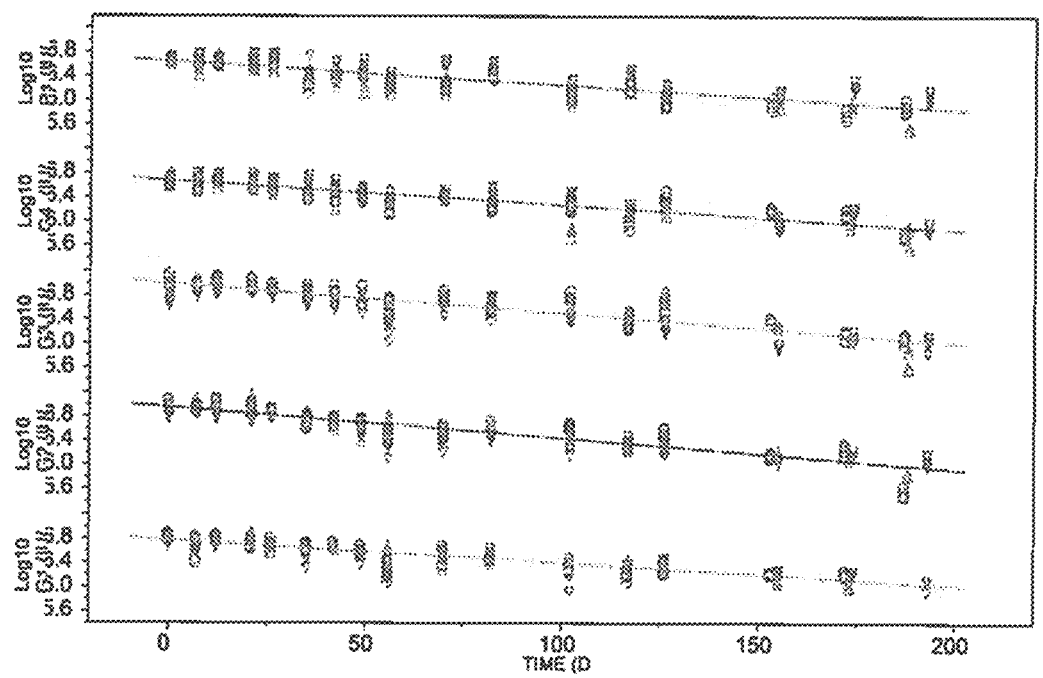
FIG. 6: Stability data of freeze dried, milled and blended formulation 1004c containing five human bovine serotypes (G1, G2, G3, G4 and P1) for N=1 (○), N=2 (Δ) and N=3 (□) at 45° C. storage conditions.

The milled and blended freeze dried exemplified formulation 1004c was aliquoted into type-I glass vials and stored at 37° C.±2° C. (RH 75%±5%) and 45° C.±2° C. (RH 75%± 5%). At the time of sampling, the freeze dried vaccine is reconstituted with the reconstitution buffer followed by potency analysis. Process loss is calculated as a difference of potency between samples before and after freeze drying in three independent manufacturing batches. Stability loss is calculated by linear regression of potency data of samples incubated at this storage condition for at least 26 weeks.

i. Exemplified formulation 1004c exhibited cumulative potency losses that are reproducibly statistically equal to 0.0 even after 26 weeks at 2° C. to 8° C. storage conditions as shown in FIG. 4.

ii. Exemplified formulation 1004c exhibited cumulative potency losses that are significantly and reproducibly lower than 0.5 log even after 26 weeks at 37° C.±2° C. (RH 75%±5.0%) storage conditions as shown in FIG. 5.

iii. In case of 45° C.±2° C. (RH 75%±5%) storage conditions, the potency values reproducibly reached equal to 0.5 log loss; for three independent manufacturing batches within 18 weeks as shown in FIG. 6.

Study 7: Post Reconstitution Stability Studies for Lead Formulation 1004c

The freeze dried pentavalent rotavirus vaccine is reconstituted with the reconstitution buffer. Aliquots of 200 μL

We claim:

1. A thermostable freeze dried rotavirus vaccine formulation wherein said vaccine formulation comprises
   at least one rotavirus serotype, and
   at least one excipient comprising a lyoprotectant, a first class of buffering agent, a bulking agent, and an activating agent, and optionally a salt, an ion and/or a dispersant wherein the lyoprotectant is selected from sucrose, trehalose, sorbitol, and lactose, either alone or in combination;

the first class of buffering agent is selected from HEPES, Tris, phosphate, citrate, and Histidine, either alone or in combination;

if present, the salt is selected from Sodium chloride, Magnesium chloride, and Potassium chloride, either alone or in combination;

if present, the ion is selected from Zn(II) or Ca (II) either alone or in combination;

the bulking agent is selected from Polyvinylpyrrolidone (PVP), Dextran, and mannitol, either alone or in combination;

if present, the dispersant is polysorbate 20 and/or polysorbate 80; and the activating agent is L-Arginine and/or Glycine, wherein said lyoprotectant is in the range of 1.2% w/v to 6.0% w/v said first class of buffering agent is in the range of 10 mM to 50 mM;

said salt is in the range of 0 mM-50 mM;

said divalent cation is in the range of 0 mM to 2 mM;

said bulking agent is in the range of 2% to 6% w/v;

said dispersant is in the range of 0 to 0.025% w/v; and said activating agent is in the range of 10 to 100 mM.

2. The thermostable freeze dried rotavirus vaccine formulation as claimed in claim 1 wherein said lyoprotectant is Sucrose, Trehalose or a combination thereof;

said first class of buffering agent is HEPES;
said salt is Sodium Chloride (NaCl);
said divalent cation is $Ca^{+2}$;
said first class of bulking agent is PVP;
said dispersant is polysorbate 20; and
said activating agent is L-Arginine and/or Glycine.

3. The thermostable freeze dried rotavirus vaccine formulation as claimed in claim 1 wherein said rotavirus serotype is selected from at least one rotavirus strain selected from bovine, rhesus, human, ovine, rhesus/human reassortants, bovine/human reassortants and other monovalent or multivalent rotavirus.

4. The thermostable freeze dried rotavirus vaccine formulation as claimed in claim 1 wherein said rotavirus serotype is selected from G1, G2, G3, G4 and P1 Human-Bovine reassortants either alone or in combination.

5. The thermostable freeze dried rotavirus vaccine formulation as claimed in claim 4 wherein said rotavirus serotype having $Log_{10}$ concentration as G1: 6.81, G2: 6.92, G3: 6.91, G4: 6.78 and P1: 6.83 per dose.

6. The thermostable freeze dried rotavirus vaccine formulation as claimed in claim 1 wherein said vaccine formulation does not exceed potency losses exceeding $Log_{10}=[0.5]$ when stored at 5 +/−3° C. up to 2 years and when stored up to 45° C. for at least 18 weeks.

7. An improved freeze drying process of preparing thermostable freeze dried rotavirus vaccine formulation as claimed in claim 1, said process comprising the steps of:
    (a) selecting at least one rotavirus serotype;
    (b) selecting said at least one excipient;
    (c) adding said selected rotavirus serotype of step (a) to said at least one excipient of step (b) to prepare a liquid feed with optimal potency retention;
    (d) freeze drying said aqueous liquid feed of step (c) to obtain a freeze dried formulation;
    (e) milling said freeze dried formulation obtained from step (d) by using suitable milling methods at temperatures ranging from 0° C. to 25° C. to obtain a milled dried formulation; and
    (f) blending of said milled dried formulation obtained from step (e) with a blending agent individually or in combination with a second class of buffering agent having acid neutralizing capacity to obtain said thermostable freeze dried rotavirus vaccine formulation for appropriate packaging of monodose or multidose, wherein the process results in a potency loss not exceeding $Log_{10}=[0.2]$.

8. The improved freeze drying process of preparing thermostable freeze dried rotavirus vaccine formulation as claimed in claim 7 wherein said liquid feed is having solid contents in the range of 10 g/100 ml to 25 g/100 ml.

9. The improved freeze drying process of preparing thermostable freeze dried rotavirus vaccine formulation as claimed in claim 7 wherein said freeze drying process is performed either at clinically relevant specification (1×) or at higher (5×) rotavirus concentrations.

10. The improved freeze drying process of preparing thermostable freeze dried rotavirus vaccine formulation as claimed in claim 7 wherein said liquid feed is having titre value in the range of 5.0E+06 IU/mL to 6.0E+07 IU/mL each serotype, preferably 5.0E+06 IU/mL to 4.0E+07 IU/mL each serotype.

11. The improved freeze drying process of preparing thermostable freeze dried rotavirus vaccine formulation as claimed in claim 7 wherein said freeze drying process results in cumulative potency loss not exceeding $Log_{10}=[0.5]$ at temperature in the range of 37° C. +/−2° C. for at least 30, 60, 90, 180 days and $Log_{10}=[0.5]$ at temperature in the range of 45° C. +/−2° C. for at least 30, 60, 90, 120 days.

12. The improved freeze drying process of preparing thermostable freeze dried rotavirus vaccine formulation as claimed in claim 7 wherein said milled freeze dried powder is obtained by milling methods including Sieve milling, Hammer milling, Ball milling, Conical sieve milling and Roller milling wherein,
    Particle size of said milled freeze dried powder have $D_{90}$ value, is not less than 250 μm;
    the preferred temperature range is in range of 20° C.-22° C.; and
    said milling is performed in presence of a dry gas including Nitrogen, Argon, $CO_2$, air or combinations thereof.

13. The improved freeze drying process of preparing thermostable freeze dried rotavirus vaccine formulation as claimed in claim 7 wherein said vaccine formulation is in dry form such as freeze dried cake, freeze dried powder, milled freeze dried powder, milled and blended freeze dried powder.

14. The improved freeze drying process of preparing thermostable freeze dried rotavirus vaccine formulation as claimed in claim 12 wherein said milled freeze dried powder shows glass transition temperature ($T_g$) in the range of 48.0 +/31 1.0° C.

15. The improved freeze drying process of preparing thermostable freeze dried rotavirus vaccine formulation as claimed in claim 7 wherein said residual moisture content of said freeze dried rotavirus vaccine formulation is below 3.0%.

16. The improved freeze drying process of preparing thermostable freeze dried rotavirus vaccine formulation as claimed in claim 9 wherein said blending agent is selected from PVP K25, PVP K40, sucrose, mannitol, maltodextrin with DE ranging from 4 to 20, fructose, glucose, lactose either alone or in the combinations providing $D_{90}$ >250 μm to milled blended freeze dried powder.

17. The improved freeze drying process of preparing thermostable freeze dried rotavirus vaccine formulation as claimed in claim 7 wherein said second class of buffering agent being selected from HEPES, Trisodium citrate dihydrate, histidine, calcium carbonate, sodium carbonate, potassium carbonate, sodium bicarbonate, calcium bicarbonate, potassium bicarbonate, aluminum hydroxide, sodium dihydrogen phosphate monohydrate or magnesium hydroxide or combinations thereof.

18. The improved freeze drying process of preparing thermostable freeze dried rotavirus vaccine formulation as claimed in claim 7 wherein said second class of buffering agent when used in conjunction with blending agent results in said acid neutralization capacity of the vaccine in the range of 0.3 mEq/dose to 1.0 mEq/dose of powder.

19. The improved freeze drying process of preparing thermostable freeze dried rotavirus vaccine formulation as claimed in claim 7 wherein said vaccine is administered orally with or without a reconstitution buffer or with or without water for injection.

20. The improved freeze drying process of preparing thermostable freeze dried rotavirus vaccine formulation as claimed in claim 19 wherein said reconstitution buffer is selected from calcium carbonate, sodium carbonate, potassium carbonate, sodium bicarbonate, calcium bicarbonate, potassium bicarbonate, aluminum hydroxide or magnesium hydroxide, sodium dihydrogen phosphate monohydrate, trisodium citrate dihydrate, phosphate citrate, or combinations thereof.

21. The improved freeze drying process of preparing thermostable freeze dried rotavirus vaccine formulation as claimed in claim 20 wherein said vaccine formulation when reconstituted with reconstitution buffer results in acid neutralizing capacity in the range of 0.3 mEq/dose to 1.0 mEq/dose.

22. The improved freeze drying process of preparing thermostable freeze dried rotavirus vaccine formulation as claimed in claim 21 wherein the palatability of said reconstitution buffer is maintained by adding 0-60% of sugars such as lactose, glucose, sucrose, fructose or the combinations thereof.

23. The improved freeze drying process of preparing thermostable freeze dried rotavirus vaccine formulation as claimed in claim 7 further comprising the step of:
(a) packaging of said thermostable freeze dried rotavirus vaccine formulation in a container along with said reconstitution buffer comprising said buffering agent having said acid neutralizing capacity in a separate container for reconstitution prior to oral administration.

24. The improved freeze drying process of preparing thermostable freeze dried rotavirus vaccine formulation as claimed in claim 20 wherein said vaccine when reconstituted with said reconstitution buffer maintains virus potency losses not exceeding $Log_{10}=[0.5]$ at storage conditions of 2° C.-8° C. for 48 h and 25° C. for 8 h.

25. The improved freeze drying process of preparing thermostable freeze dried rotavirus vaccine formulation as claimed in claim 7 wherein said vaccine formulation dissolves within 60 +/−5.0 sec in said reconstitution buffer maintained at 23° C. +/−1° C.

26. The improved freeze drying process of preparing thermostable freeze dried rotavirus vaccine formulation as claimed in claim 7, wherein step (d) is performed in vials or in trays.

27. The improved freeze drying process of claim 7, wherein the solid content of liquid feed is 13 g/100 ml (13%).

* * * * *

UNITED STATES PATENT AND TRADEMARK OFFICE
CERTIFICATE OF CORRECTION

| | |
|---|---|
| PATENT NO. | : 10,532,093 B2 |
| APPLICATION NO. | : 15/327142 |
| DATED | : January 14, 2020 |
| INVENTOR(S) | : D Gill et al. |

It is certified that error appears in the above-identified patent and that said Letters Patent is hereby corrected as shown below:

On the Title Page

Item (73), The assignee name should be corrected to read "MSD WELLCOME TRUST HILLEMAN LABORATORIES PVT. LTD."

Signed and Sealed this
Twenty-third Day of June, 2020

Andrei Iancu
*Director of the United States Patent and Trademark Office*